United States Patent [19]
Paik et al.

[11] Patent Number: 6,010,898
[45] Date of Patent: Jan. 4, 2000

[54] **LIQUID CULTIVATION OF STRAINS OF *BACILLUS POLYFERMENTICUS***

[75] Inventors: Hyun Dong Paik, Changwon; Kyung Dong Jeon, Pusan; Seung Hee Sung, Pusan; Won Seok Kim, Pusan; Hyun Soo Kim, Pusan; Baek Chun Lee, Pusan, all of Rep. of Korea

[73] Assignee: Soonchundang Pharmaceuticals Co., Ltd., Pusan, Rep. of Korea

[21] Appl. No.: 09/018,940

[22] Filed: Feb. 5, 1998

[30] Foreign Application Priority Data

Sep. 13, 1997 [KR] Rep. of Korea .................. 97-47382

[51] Int. Cl.$^7$ ................................... C12N 1/20
[52] U.S. Cl. ............................ 435/252.5; 435/832
[58] Field of Search .................. 435/252.5, 832

[56] References Cited

U.S. PATENT DOCUMENTS

| | | | |
|---|---|---|---|
| 3,661,715 | 5/1972 | Bonnat et al. | 195/66 R |
| 4,374,981 | 2/1983 | Tsuda et al. | 536/24 |
| 5,639,658 | 6/1997 | Drobis et al. | 435/243 |

FOREIGN PATENT DOCUMENTS 11123  1/1936  Japan .

OTHER PUBLICATIONS

Atlas R.M. Handbook of Microbiological Msdia. Ed. L.C. Parks. CRS Press, 1993, pp. 264–265.

Japanese Pharmaceutical Cdex 1993—Medicine Composition Standard, pp. 1005–1007.

Bergey's of Systematic Bacteriology 1st cd.—Endospore–forming Gram–Positive Rods and Cocci (P. Sneath), pp. 1104–1139. 1986.

Biochemical Tests For Identification Of Medical Bacteria, 2nd Edition. 1985. (J. MacFaddin): Citrate test, pp. 59–63; Gelatin Liquefaction test, pp. 128–137; Gluconate test, pp. 137–141; Nitrate Reduction test, pp. 236–245; Starch Hydrolysis test, pp. 289–298; Voges– proskauer test, pp. 308–320; pp. 345–369; pp. 371–438.

Manual For The Identification of Medical Bacteria (Cowan and Steel), pp. 45–122. 1984.

*Primary Examiner*—Irene Marx
*Assistant Examiner*—Vera Afremova
*Attorney, Agent, or Firm*—McAulay Nissen Goldberg Kiel & Hand, LLP

[57] ABSTRACT

Disclosed herein is a process for cultivating the strains of *Bacillus polyfermenticus*, which is a beneficial endospore forming bacteria. The process includes an use of certain culture medium containing inexpensive ingredients and is carried out in a fed-batch manner. It allows a significant increase of the yield of the cultivation. In particular, the process for cultivating *Bacillus polyfermenticus* strain SCD KCCM 10104 is disclosed.

1 Claim, No Drawings

LIQUID CULTIVATION OF STRAINS OF BACILLUS POLYFERMENTICUS

BACKGROUND OF THE INVENTION

1. Field of the Invention

The present invention is related to a cultivation of strains of *Bacillus polyfermenticus*. More particularly, the present invention is related to a large-scale production of *Bacillus polyfermenticus* strains in an economic way with a high yield.

2. Description of the Prior Arts

Beneficial bacteria, which have been used for medical purpose and for medicines for treating intestinal disorders, include strains of Bifidobacterium, Lactobacillus, Enterococcus, *Clostridium butyricum, Lactobacillus sporogenes, Bacillus subtilis, Bacillus polyfermenticus* and the like. In particular, *B. Polyfermenticus* which is commonly called as "Bispan" strains, have been appropriately used for the treatment of long-term intestinal disorders, since the live strains in the form of active endospores can successfully reach the target intestine.

Bispan strains are stated in Japanese Pharmacopoeia as a amylolytic bacillus along with *Bacillus subtilis* and *Bacillus mesentericus*. See Japanese Pharmacopoeia, Medicine Composition Standard Standard 1005–1007 (1993). However, the term "Bispan" does not appear in the International Nomenclature such as Bergey's Manual of Systematic Bacteriology (Sneath, P.H.A.: Endospore-forming gram-positive rods and cocci. In Bergey's Manual of Systematic Bacteriology 1st ed. 1104–1139, Williams & Wilkins, Baltimore (1986)). Several studies suggested that the Bispan strains are significantly similar to *Bacillus subtilis* strains in terms of morphological and biochemical properties. However, the Bispan strains are still distinct from *Bacillus subtilis* strains that the former is capable of metabolizing lactose and produces a larger amount of acetic acid and lactic acid from glucose and lactose, respectively, than the latter does.

The Bispan strain, a endospore-forming rod, was for the first time isolated from air by Dr. Terakado in 1933. It produces a variety of enzymes which lysis pathogenic strains such as typhoid bacillus, paratyphoid bacillus, shigella, cholera. The uptake of the Bispan strains can enhance the appetite and promote digestion action in the human by serving as vitamin $B_1$ and $B_2$ sources as well as strengthens the protection from non-oral infection and oral immunization.

The cultivation and application of the Bispan strain was described in Japanese patent publication No. sho 11–123 "A process for manufacturing medicine for intestine disorders by using bacteria." It teaches that the medicine for intestine disorders are manufactured by carrying out four (4) cycles of procedure consisted of heating a Bispan culture after the cultivation to 65° C. for 1 hour, allowing to stand the heated culture at 33° C. for 24 hours and then heating it to 65° C. for 1 hour; making the culture weak acidic using acetic acid and dehydrating it under an elevated temperature; adding 0.3–0.5% azueous sulfuric acid and allowing the mixture to stand at 37° C.; dehydrating the mixture under an elevated temperature; and adding a certain amount of starch and lactose to the thus-treated mixture to produce the medicine for intestinal disorders.

The known cultivation of Bispan strain has a shortcoming that it requires too many steps to harvest the cells from the culture, resulting in an increase of the production cost. Further, it uses a very expensive culture medium such as Bouillon medium.

Therefore, it had been needed a large-scale process for cultivating the Bispan strain and harvesting its endospores with a high yield in an economic way.

SUMMARY OF THE INVENTION

Thus, an object of the present invention is to provide a large-scale process for cultivating *Bacillus polyfermenticus*.

Another object of the present invention is to increase the number of endospores of *Bacillus polyfermenticus* contained in its culture.

These objects and other objects of the present invention can be accomplished by a process for cultivating *Bacillus polyfermenticus*, which comprises the steps of:

placing an inoculum of *Bacillus polyfermenticus* SCD strain into a liquid production medium comprising (a) one or more elements selected from the group consisting of 1–3% by weight of glucose, 1–5% by weight of corn starch, 1–5% by weight of soybean flour and 2–20% by weight of corn steep liquor; and (b) trace elements comprising 0.05–0.5% by weight of monopotassium phosphate, 0.05–0.5% by weight of dipotassium phosphate, 0.05–0.5% by weight of calcium chloride·$2H_2O$, 0.01–0.1% by weight of magnesium sulfate·$7H_2O$, 0.001–0.01% by weight of copper sulfate·$5H_2O$, 0.001–0.01% by weight of manganese sulfate, 0.001–0.01% by weight of ferric sulfate·$7H_2O$ and 0.001–0.01% by weight of zinc sulfate·$7H_2O$; and cultivating the strain at an aerobic condition at a temperature of 30°–37° C. and pH of 6.8–7.2.

The present invention also provides a cultivation process, wherein the liquid production medium is prepared by dissolving and mixing 1–3% by weight of glucose, 1–5% by weight of corn starch, 5–20% by weight of corn steep liquor, and the trace elements in a distilled water.

The present invention still provides a cultivation process, wherein the liquid production medium is prepared by dissolving and mixing 1–3% by weight of glucose, 1–5% by weight of soybean flour, and the trace elements in a distilled water.

The present invention further provides a cultivation process, wherein the liquid production medium is prepared by dissolving and mixing 1–3% by weight of glucose, 1–3% by weight of corn starch, 2–10% by weight of corn steep liquor, 1–3% by weight of soybean flour, and the trace elemnts in a distilled water.

The above and other objects, features and applications of the present invention will be apparent to those of ordinary skill in the art from the following detailed explanation.

DETAILED EXPLANATION OF THE INVENTION

For the present invention, we determined an optimum composition of culture medium for the *Bacillus polyfermenticus* strains, which is advantageous in the light of economic viewpoint and the efficiency. Further, we established an optimum cultivation condition for the *Bacillus polyfermenticus* strains.

In the present invention, the number of total live strains is calculated by continuously diluting the culture with 0.1% (W/V) peptone water, streaking 0.1 ml of the diluted culture on a agar plate in a petri dish, and culturing 35° C. for 24 hours followed by counting the number of cfu(colony forming unit). And, the number of active endospores is calculated by killing vegetative cells by heating the culture at 80° C. for 2 hours, continuously diluted with a sterile diluent, placing 0.1 ml of the diluted culture on TSA (Tryptic soy agar) plate medium, overlaying with a soft agar, and culturing at 37° C. for 24 hours followed by counting the number of cfu.

The culture broth containing endospores of *Bacillus polyfermenticus* can be formulated into powders or liquids by using common methods. For example, the powder formulation can be prepared by spray drying or freeze drying techniques. The spray drying technique may include an addition of sticking agents, stabilizers, diluents, and the like, all of which are well known to the ordinary skilled in the art. The kind and amount of these additives can be readily determined by the ordinary skilled depending on the kind or usage of the formulations.

The present invention will be described in more detail by way of various Example, which shall not be construed to limit the scope of the invention. In the Examples, the % is based on the weight, unless otherwise indicated.

Reference Example 1

Since any isolate established strain or endospores of *Bacillus polyfermenticus* is not commercially available nor cannot be provided from the depositary, we first obtained an isolate *Bacillus polyfermenticus* strain from the commercially available medicine product containing its endospores.

Thus, 0.1 ml of the medium diluted with a small amount of the powder of Bisroot tablet® was streaked on nutrient agar or tryptic soy agar in petri dish and cultured at 37° C. Colonies having different shape, color or surface characteristics were selected and pure cultured by using dilution method. Each colony was tested using Gram staining, Malachite Green spore staining and flagella staining with an aid of microscope. Biochemical properties and activities were tested based on Biochemical test for Identification of medical bacteria; Manual for the Identification of medical bacteria. Based on the comparison of the isolates with the known *Bacillus polyfermenticus*, which was reported in Japan, a colony having the same characteristics as those of the known *Bacillus polyfermenticus* was isolated.

Thus isolated strain was named as *Bacillus polyfermenticus* SCD, and deposited under Budapest Treaty with KCCM (Korea Culture Center of Microorganisms) on Aug. 5, 1997 and given an accession number of KCCM 10104.

The characteristics of *Bacillus polyfermenticus* SCD are summarized in Table 1, together with those of known *Bacillus polyfermenticus*.

TABLE 1

| Characteristics | *Bacillus polyfermenticus* SCD (KCCM 10104) | Known *Bacillus polyfermenticus* |
|---|---|---|
| Morphology | Rod | Rod |
| Gramstaining | Positive | Positive |
| Motility | Yes | Yes |
| Endospore formation | Yes | Yes |
| Oxygen requirement | Aerobic | Aerobic |
| Acid formation from glucose | Yes | Yes |
| Starch hydrolysis | Yes | Yes |
| Gelatin hydrolysis | Yes | Yes |
| Casein hydrolvsis | Yes | Yes |
| Voges-Proskauer Test | Positive | Positive |
| Nitrate reduction | Yes | Yes |
| Citric acid availability | Yes | Yes |

EXAMPLE 1

Strain used: *Bacillus polyfermenticus* SCD (KCCM 10104)

Seed cultivation: One loopful of inoculum of *Bacillus polyfermenticus* SCD was placed in TSB (Tryptic soy both) medium in a 500 ml baffled flask, and the seed cultivation was carried out at 37° C. while shaking at 200 rpm for about 10 hours.

Composition of production medium and its preparation:

| | |
|---|---|
| Glucose | 20 g/L |
| Corn starch | 10 g/L |
| Soybean flour | 30 g/L |
| Trace elements: | |
| Monopotassium phosphate | 1 g/L |
| Dipotassium phosphate | 1 g/L |
| Calcium chloride · $2H_2O$ | 0.1 g/L |
| Magnesium sulfate · $7H_2O$ | 0.3 g/L |
| Copper sulfate · $5H_2O$ | 0.01 g/L |
| Manganese sulfate | 0.02 g/L |
| Ferric sulfate · $7H_2O$ | 0.02 g/L |
| Zinc sulfate · $7H_2O$ | 0.02 g/L |

All ingredients of the medium were sterilized before introducing the fermenter. Thus, the heat-stable elements such as corn starch, soybean flour and calcium chloride·$2H_2O$ were sterilized using an autoclave at 121° C. for 20 minutes. Beside, the remaining heat-labile ingredients or complex-forming ingredients were sterilized by passing through a disposable membrane filter having a pore size of 0.45 μm.

Cultivation: The seed culture (30–60 ml) was placed into 3 liter of the above-described production medium in a 5 liter fermenter. The cultivation was carried out at 37° C. under aeration of 1.0 vvm. The agitation speed was 500–700 rpm. After 72–96 hours from the inoculation, the cultivation was stopped.

The yield of the cultivation can be increased by employing the fed-batch process. That is to say, during the initial stage of the cultivation, when the complete consumption of glucose is observed, a sterile concentrated glucose was supplied to a final concentration of about 1% into the culture, resulting in an increase of about 58% of the number of maximum active endospores compared to batch cultivation, as shown in Table 2.

TABLE 2

| Cultivation | No. of Active Endospores in cfu/ml | |
|---|---|---|
| Time (hr) | Batch cultivation | Fed-batch cultivation |
| 24 | $1.70 \times 10^8$ | $1.95 \times 10^8$ |
| 36 | $6.55 \times 10^8$ | $8.24 \times 10^8$ |
| 48 | $1.80 \times 10^9$ | $2.20 \times 10^9$ |
| 60 | $2.17 \times 10^9$ | $4.26 \times 10^9$ |
| 72 | $2.34 \times 10^9$ | $5.10 \times 10^9$ |
| 96 | $3.28 \times 10^9$ | $5.20 \times 10^9$ |
| 120 | $2.96 \times 10^9$ | $5.20 \times 10^9$ |

EXAMPLES 2–4

The procedure of Example 1 was repeated except that the composition of the production medium was as shown in Table 3.

TABLE 3

| Composition | Example 2 | Example 3 | Example 4 |
| --- | --- | --- | --- |
| Glucose | 20 g/L | 20 g/L | 30 g/L |
| Corn starch | 10 g/L | – | 20 g/L |
| Corn steep liquor | 100 ml/L | – | 40 ml/L |
| Soybean flour | – | 25 g/L | 15 g/L |
| Trace elements | + | + | + |

In addition to the fed-batch cultivation as described in Example 1, a batch cultivation using the same production medium was carried. The maximum cultivation using the same production medium was carried. The maximum number of endospores of *Bacillus polyfermenticus* was calculated and is shown in Table 4.

TABLE 4

| Example | Maximum No. of active endospore in cfu/ml | | Increase Rate (%) |
| --- | --- | --- | --- |
| | Batch | Fed-batch | |
| 2 | $2.80 \times 10^9$ | $4.25 \times 10^9$ | 51.0 |
| 3 | $2.40 \times 10^9$ | $4.10 \times 10^9$ | 70.8 |
| 4 | $3.10 \times 10^9$ | $4.84 \times 10^9$ | 56.1 |

EXAMPLE 5

To evaluate the effect of the medium according to the present invention, a batch cultivation using either the medium of Example 1 or TSB (Tryptic soy broth) medium was carried out by following the procedure in Example 1. The maximum number of endospores of *Bacillus polyfermenticus* was calculated and is shown in Table 5.

TABLE 5

| Culture medium | Maximum No. of active endospores in cfu/ml | Productivity |
| --- | --- | --- |
| TSB | $1.71 \times 10^9$ | $5.7 \times 10^8$ cfu/ml/day |
| Example 1 | $3.28 \times 10^9$ | $8.2 \times 10^8$ cfu/ml/day |

The results in Table 5 show that the use of the medium according to the present invention allows an increase of the yield of approximately 44%.

EXAMPLE 6

To evaluate the effect of the medium according to the present invention, a fed-batch cultivation using either the medium of Example 1 or TSB (Tryptic soy broth) medium was carried out by following the procedure in Example 1. thus, after complete consumption of glucose in the culture, a concentrated glucose was supplied into the culture to a final concentration of 1%, which was repeated several times during the cultivation. The maximum number of endospores of *Bacillus polyfermenticus* was calculated and is shown in Table 6.

TABLE 6

| Culture medium | No. of maximum Active endospore in cfu/ml | Productivity |
| --- | --- | --- |
| TSB | $2.05 \times 10^9$ | $6.8 \times 10^8$ cfu/ml/day |
| Example 1 | $5.20 \times 10^9$ | $13.0 \times 10^8$ cfu/ml/day |

The results in Table 6 show that the use of the medium according to the present invention in the fed-batch cultivation allows an increase of the yield of approximately 90%.

Accordingly, the present invention allows a significant increase of the cultivation yield while employing a non-expensive medium.

Although preferred embodiments of the present invention have been described in detail hereinabove, it should be clearly understood that many variations and/or modifications of the basic inventive concepts herein taught which may appear to those skilled in the art will still fall within the spirit and scope of the present invention as defined in the appended claims.

What is claimed is:

1. A process for cultivating *Bacillus polyfermenticus,* which comprises the steps of:

(1) preparing a fermentation mixture by placing an inoculum of *Bacillus polyfermenticus* strain SCD KCCM10104 into a liquid production medium comprising:

(a) 1–3% by weight of glucose;

(b) 1–5% by weight corn starch and, 1–5% by weight of soybean flour, and (c) trace elements comprising 0.05%–0.5% by weight of monopotassium phosphate, 0.05–0.5% by weight of dipotassium phosphate, 0.05–0.5% by weight of calcium chloride·2H$_2$O, 0.01–0.1% by weight of magnesium sulfate·7H$_2$O, 0.001–0.01% by weight of copper sulfate·5H$_2$O, 0.001–0.01% by weigght of manganese sulfate, 0.001–0.01% by weight of ferric sulfate·7H$_2$O and 0.001–0.01% by weight of zinc sulfate·7H$_2$O;

(2) cultivating the strain in the fermentation mixture under aerobic conditions at a temperature of 30°–37° C. and pH of 6.8–7.2, in a fed-batch manner wherein after the glucose in the fermentation mixture is completely consumed, supplying additional glucose to bring the concentration of glucose in the fermentation mixture to 1%; and (3) recovering *Bacillus polyfermenticus* strain SCD KCCM 10104 cells from the fermentation mixture.

* * * * *